United States Patent [19]
Duer

[11] Patent Number: 5,669,879
[45] Date of Patent: Sep. 23, 1997

[54] CATHETER ASSEMBLY FOR DILATION OF CONSTRICTED BLOOD VESSEL

[76] Inventor: Edward Yeend Duer, 31-2, Mekamiyama-cho, Koyoen, Nishinomiya-city, Hyogo-pref., Japan

[21] Appl. No.: 259,982

[22] Filed: Jun. 15, 1994

[51] Int. Cl.$^6$ ............................................ A61M 29/00
[52] U.S. Cl. ........................ 604/96; 604/97; 606/192
[58] Field of Search ............ 604/96–103; 606/192–196; 600/18; 128/207.15

[56] References Cited

U.S. PATENT DOCUMENTS

| | | | |
|---|---|---|---|
| 1,014,228 | 1/1912 | Kellogg | 604/99 |
| 3,049,125 | 8/1962 | Kriwkowitsch | 604/100 |
| 4,364,392 | 12/1982 | Strother et al. | 604/98 X |
| 4,758,223 | 7/1988 | Rydell | 604/98 |
| 4,793,351 | 12/1988 | Landman et al. | 604/99 |
| 4,813,935 | 3/1989 | Haber et al. | 604/99 |
| 4,856,510 | 8/1989 | Kowalewski. | |
| 4,955,905 | 9/1990 | Reed | 623/8 |
| 5,254,092 | 10/1993 | Polyak | 604/99 |

FOREIGN PATENT DOCUMENTS

| 971457 | 7/1975 | Canada | 604/99 |
|---|---|---|---|

*Primary Examiner*—Corrine M. McDermott
*Assistant Examiner*—Bhisma Mehta
*Attorney, Agent, or Firm*—Roy A. Ekstrand

[57] ABSTRACT

A catheter assembly for dilation of constricted blood vessels includes a catheter supporting a radiopaque balloon insertable into a patient blood vessel. The catheter provides a coupling passage between the inflatable radiopaque balloon and a three-way valve. The three-way valve is selectively coupled to a liquid feed mechanism such as a conventional syringe and an expandable pressure buffering balloon. The communication between the expandable radiopaque balloon and the liquid feed mechanism or pressure buffering balloon is controlled by switching the three-way valve.

9 Claims, 1 Drawing Sheet

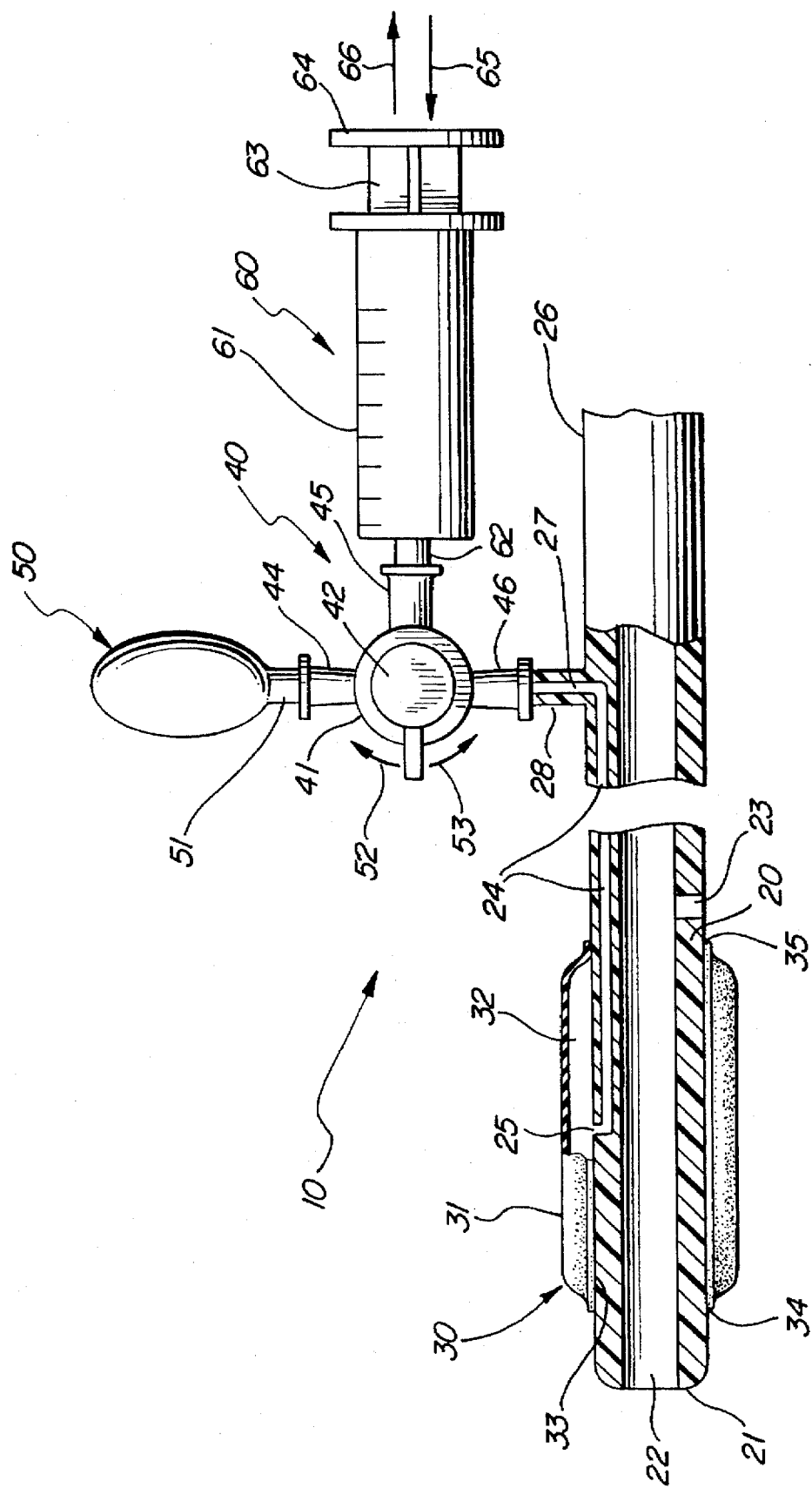

CATHETER ASSEMBLY FOR DILATION OF CONSTRICTED BLOOD VESSEL

FIELD OF THE INVENTION

This invention relates generally to blood vessel catheters and particularly to those used in the dilation of constricted blood vessel areas.

Background of the Invention

One of the more life threatening problems which afflict human blood circulatory systems is the tendency for constrictions to form within blood vessels through the formation of an atheroma or accumulation of plaque. Such constrictions left untreated reduce or restrict and in more severe cases block the flow of fresh blood supply to the heart or other tissues. The end result is severe pain and/or heart attack. One of the most conventional treatment options available to practitioners in the art is referred to as percutaneous translumenal coronary angioplasty (or PTCA). In this procedure, an imaging agent comprising a liquid exhibiting a high opacity to X-ray energy is preinjected into a blood vessel such that the radiopaque material or dye is carried into the portion of the blood vessel in which the constriction has formed. Thereafter, X-ray fluoroscopy is used to locate and identify the nature and extent of the constriction. Thereafter, a catheter supporting an inflatable balloon is inserted into an appropriate portion of the blood vessel system and carefully moved within the blood vessel to position the balloon at the constriction. Once the catheter and balloon are properly positioned and observed using further X-ray fluoroscopy, an imaging agent diluted with normal saline is then injected into the balloon during continued X-ray fluoroscopy causing the balloon to inflate and dilate the constricted portion of the blood vessel with the objective of restoring normal blood flow.

Conventional balloon catheters for dilation of constricted blood vessels have proven difficult to use due in part to the difficulties of injecting an imaging agent into the blood vessel and to pass the diluted imaging agent and saline solution through the fine passages within the catheter lumen. In addition, it has been shown that substantial risk of undesirable side effects arise in the use of conventional angioplasty procedures.

Thus, despite the frequent use and reliance of medical practitioners upon conventional angioplasty procedures, there remains nonetheless a continuing need in the art for evermore improved systems for dilation of constricted blood vessels which avoid the above-mentioned problems and which reduce the extent of risk imposed upon the patient.

SUMMARY OF THE INVENTION

Accordingly, it is a general object of the present invention to provide an improved catheter assembly for dilation of constricted blood vessels. It is a more particular object of the present invention to provide an improved catheter assembly for dilation of constricted blood vessels which avoids the need for subjecting the patient to the substantial risks associated with the use of radiopaque imaging materials or dyes. It is a still more particular object of the present invention to provide an improved catheter assembly for dilation of constricted blood vessels which minimizes the interference with blood flow during the procedure.

In accordance with the present invention, there is provided for use in dilating a constricted blood vessel, a catheter assembly comprises: a catheter defining a blood vessel insertable end, a remote end, and a lumen passage having a first outlet proximate the insertable end and a second outlet spaced from the insertable end; a radiopaque balloon supported upon the insertable end and coupled to the first outlet of the lumen passage, the radiopaque balloon having at least a portion characterized by radiopaque properties; an expandable pressure reservoir; a source of liquid under pressure; and valve means coupled to the second outlet of the lumen passage, the expandable pressure reservoir and the source of liquid under pressure, the valve means being capable of alternatively intercoupling the source of liquid to the expandable pressure reservoir, or the source of liquid to the second outlet of the lumen or the expandable pressure reservoir to the second outlet of the lumen passage.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawing in which:

The FIGURE sets forth a partial section view of a catheter assembly for dilation of constricted blood vessel constructed in accordance with the present invention.

DESCRIPTION OF THE PREFERRED EMBODIMENT

The drawing sets forth a partially sectioned view of a catheter assembly constructed in accordance with the present invention and generally referenced by numeral 10. Catheter assembly 10 includes an elongated generally cylindrical catheter tube 20 having an insertable end 21 and a remote end 26. Catheter tube 20 is fabricated of a flexible material and defines a center passage 22 extending between end 21 and remote end 26. Catheter tube 20 further defines a blood bypass port 23 extending between the exterior surface of catheter tube 20 and center passage 22. Catheter tube 20 further defines a fitting 28 extending outwardly near remote end 26 and a lumen passage 24 extending longitudinally through one wall portion of catheter tube 20. Lumen passage 24 terminates in an outwardly facing outlet 25 proximate end 21 and an outlet 27 extending through fitting 28.

A radiopaque balloon 30, formed to include preferably an interior surface or composed of or blended with a radiopaque material such as gold, iron, platinum, barium or the like includes a flexible outer skin 31 surrounding an interior cavity 32. Outer skin 31 defines a generally cylindrical passage 33 encircling the outer surface of catheter tube 20 proximate end 21. Catheter tube 20 extends through passage 33 via an aperture 35 at one end of passage 33 and an aperture 34 at the other end of passage 33. Interior cavity 32 of radiopaque balloon 30 is preferably coated with one or more of the above-identified radiopaque materials and communicates with outlet 25 of lumen passage 24 to provide a fluid flow coupling therebetween. In its preferred form, radiopaque balloon 30 is fabricated of a radiopaque material in a manner which imparts or maintains an elastic characteristic such as rubber or the like. Alternatively, balloon 30 may be fabricated of an inelastic plastic such as polyethylene terephthalate or polyethylene thin film. The radiopaque characteristic is provided by blending the material utilized in fabricating radiopaque balloon 30 with an X-ray blocking material such as compounds containing barium, iron, bismuth, iodine, or gold. Alternatively, the radiopaque property of radiopaque balloon 30 may be obtained by coating or depositing such materials preferably upon the interior surface of radiopaque balloon 30. It will be recognized that it is sufficient in some applications of the present invention catheter assembly to provide a portion of radiopaque balloon 30 with radiopaque properties rather than the entire body of radiopaque balloon 30. Where partial area radiopaque properties are utilized in fabricating radiopaque balloon 30, the essential aspect is the provision of a radiopaque material pattern which facilitates the determination of the balloon shape during X-ray fluoroscopy.

Catheter assembly 10 further includes a three-way valve 40 having a valve body 41 defining a plurality of fittings 44, 45 and 46. Valve 40 is constructed in accordance with conventional fabrication techniques and thus includes a rotatable valve rotor 42 having an outwardly extending tab 43. The essential function of valve 40 is to provide selective coupling between the desired ones of fittings 44, 45 and 46. Thus, in the three-way valve construction set forth as valve 40, tab 43 is movable in the directions indicated by arrows 52 and 53 to provide such selective coupling between fittings 44, 45 and 46.

Catheter assembly 10 further includes an expandable pressure reservoir 50 having a neck 51 coupled to fitting 44 and formed of an expandable preferably elastic material such as rubber or the like.

Catheter assembly 10 further includes a syringe 60 constructed in accordance with conventional fabrication techniques and defining a generally cylindrical body 61 having a forwardly extending fitting 62. Fitting 62 is coupled to fitting 45 in a fluid-type engagement. Syringe 60 further includes a movable plunger 63 having a handle 64. While not seen in the FIGURE, syringe 60 being constructed in accordance with conventional fabrication techniques includes a movable piston secured to the interior end of plunger 63 such that movement of plunger 63 and handle 64 in the direction indicated by arrow 65 produces a pressure force upon liquid within the interior of syringe body 61 forcing it outwardly through fitting 62. It will be recognized in the operation of the present invention catheter assembly set forth below that syringe 20 provides a source of liquid under pressure which may, as an alternative, be replaced by other liquid pump apparatus while nonetheless practicing the present invention. It has been found convenient, however, to utilize a conventional syringe such as syringe 60 due to the low cost thereof and the easy familiar manipulation of such syringes on the part of medical practitioners.

In operation, syringe 60 is provided with a supply of liquid such as a conventional saline solution and is coupled to fitting 45 of three-way valve 40 via fitting 62 thereof. At this point, plunger 63 extends outwardly in the direction indicated by arrow 66 from body 61 to accommodate the supply of saline solution therein. Valve 40 is then switched by moving tab 43 to provide fluid communication between fittings 44 and 45. Thereafter, plunger 63 of syringe 60 is forced inwardly into syringe body 61 to force the saline solution through fitting 45, valve 40 and fitting 44 into expandable pressure reservoir 50. Expandable pressure reservoir 50 accommodates the introduction of saline solution under pressure by expanding due to its elastic material. Thereafter, tab 43 of valve 40 is again rotated to provide coupling between fittings 45 and 46. With valve 40 in this position, plunger 63 is moved inwardly into body 61 to force saline solution through valve 40 and fittings 46 and 28 into lumen passage 24. As plunger 63 continues to be moved inwardly forcing additional saline solution through lumen passage 24, the saline solution is introduced into interior cavity 32 of radiopaque balloon 30. At this point, plunger 63 of syringe 60 is moved a relatively small amount with the objective of providing partial inflation of radiopaque balloon 30.

With radiopaque balloon 30 partially inflated, valve 40 is switched to provide coupling between fittings 44 and 46 thereby providing fluid communication between expandable pressure reservoir 50 and radiopaque balloon 30. With valve 40 thus configured and radiopaque balloon 30 partially inflated, end 21 of catheter tube 20 and radiopaque balloon 30 are inserted into the patient's blood vessel and moved forwardly therethrough. It should be noted that at this point, the partial inflation of radiopaque balloon 30 facilitates the movement of radiopaque balloon 30 and catheter tube 20 forwardly through the unconstricted blood vessel as catheter tube 20 is moved further toward the constricted portion of the blood vessel. During this movement, the communication of radiopaque balloon 30 and expandable pressure reservoir 50 permits expandable pressure reservoir 50 to provide a pressure buffer which expands to absorb pressure changes and deformation of radiopaque balloon 30.

During the insertion of catheter tube 20 and radiopaque balloon 30 into position at the target blood vessel constriction, the operation is observed by X-ray fluoroscopy and the contact with the blood vessel constriction is noted as radiopaque balloon 30 is deformed. As catheter tube 20 and radiopaque balloon 30 are moved forwardly into the constricted blood vessel portion, the pressure increase within radiopaque balloon 30 caused by deformation within the blood vessel constriction is cushioned or buffered by expandable pressure reservoir 50. Thus, as radiopaque balloon 30 is deformed to define a reduced volume, expandable pressure reservoir 50 is further expanded to absorb the pressure increase. Once again, as radiopaque balloon 30 is positioned within the constricted blood vessel area, the radiopaque character of radiopaque balloon 30 is utilized during the X-ray fluoroscopy process to properly position radiopaque balloon 30.

Once radiopaque balloon 30 is correctly positioned within the constricted blood vessel area, valve 40 is switched to provide fluid coupling between fittings 45 and 46 thereby providing fluid communication between syringe 60 and radiopaque balloon 30. With valve 40 thus positioned, plunger 63 of syringe 60 is moved inwardly into syringe body 61 forcing additional pressurized saline solution into radiopaque balloon 30 via lumen passage 24. Under the influence of additional pressurized saline solution within interior cavity 32, radiopaque balloon 30 expands outwardly and imparts an outward expanding force against the constricted portion of the blood vessel dilating the constriction and reducing or eliminating its constrictive effect upon blood flow. Once the constriction has been dilated, valve 40 is again switched to provide coupling between fittings 44 and 46 thereby providing fluid communication between radiopaque balloon 30 and expandable pressure reservoir 50. Thus, as catheter tube 20 is then removed from the constricted area, the pressure buffering action of expandable pressure reservoir 50 is provided to accommodate the removal of radiopaque balloon 30 from the constricted area. Thereafter, catheter tube 20 is removed and the procedure is completed.

It should be noted that during the dilation of the blood vessel constriction as radiopaque balloon 30 is inflated, passage 22 and bypass 23 of catheter tube 20 provide a blood flow path between each side of radiopaque balloon 30 thereby facilitating the continued blood flow during the procedure. While the provision of blood bypass port 23 is not always necessary in short duration procedures, it is extremely necessary during procedures requiring extended time.

It should be further noted that an advantage arises in the use of the present invention catheter assembly when radiopaque balloon 30 is fabricated of an inelastic material such as those mentioned above. The fabrication of radiopaque balloon 30 from an inelastic material facilitates the determination as to whether the constricted blood vessel has undergone a subsequent restenosis forming a reconstriction following dilation. The capability is provided in that radiopaque balloon 30 assumes the shape defined during the dilation of the constricted portion of the blood vessel and due to its inelasticity tends to retain the shape molded into radiopaque balloon 30 during dilation. As a result, once valve 40 is switched to couple expandable pressure reservoir 50 to radiopaque balloon 30, the buffering effect of expandable pressure reservoir 50 and inelastic characteristic of radiopaque balloon 30 cooperate to permit radiopaque balloon 30 to assume the form or shape of the restenosis should it occur. If, however, restenosis does not occur, radiopaque balloon 30 will maintain the shape established during the dilation of the blood vessel. The examination of the shape of radiopaque balloon 30 during this time by X-ray fluoroscopy permits the shape of radiopaque balloon 30 to be readily examined.

What has been shown is a catheter assembly for dilation of constricted blood vessel which utilizes a radiopaque balloon together with a source of conventional saline solution under pressure to provide expansion of the radiopaque balloon and the dilation of a constricted blood vessel area. An expandable pressure buffering balloon is selectively coupled to the radiopaque balloon to provide pressure buffering of the radiopaque balloon and the accommodation of deformation of the radiopaque balloon. The catheter assembly shown utilizes a conventional saline solution or the like to provide dilation of the constricted blood vessel area and thus avoids the undesirable use of radiopaque dye materials or the like within the patient's blood vessel system. The radiopaque character of the inflatable balloon facilitates the observation of the procedure using X-ray fluoroscopy.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in dilating a constricted blood vessel during angioplasty, athrectomy or other arterial procedures, a vascular catheter assembly comprising:
    a catheter defining a blood vessel insertable end, a remote end, and a lumen passage having a first outlet proximate said insertable end and a second outlet spaced from said insertable end;
    a radiopaque balloon formed of an inelastic material supported upon said insertable end and coupled to said first outlet of said lumen passage, said radiopaque balloon having at least a portion characterized by radiopaque properties;
    a source of liquid under pressure;
    valve means coupled to said second outlet of said lumen passage and said source of liquid under pressure, said valve means being capable of intercoupling said source of liquid to said second outlet of said lumen; and
    an expandable pressure reservoir having an inflatable elastic member,
    said valve means being coupled to said expandable pressure reservoir as well as said second outlet of said lumen passage and said source of liquid under pressure, said valve means being capable of alternatively intercoupling said source of liquid to said expandable pressure reservoir, or intercoupling said source of liquid to said second outlet of said lumen or intercoupling said expandable pressure reservoir to said second outlet of said lumen passage.

2. A catheter assembly as set forth in claim 1 wherein said source of liquid under pressure includes a syringe having a syringe body for receiving a liquid, a coupler coupled to said valve means, and a movable plunger for forcing said liquid from said syringe body through said coupler.

3. A catheter assembly as set forth in claim 2 wherein said catheter further defines a blood bypass forming a blood passage past said radiopaque balloon.

4. A catheter assembly as set forth in claim 3 wherein said catheter defines a center passage extending from said insertable end and wherein said blood bypass includes a bypass port extending through said catheter into said center passage.

5. For use in dilating a constricted blood vessel during angioplasty, athrectomy or other arterial procedures, a vascular catheter assembly comprising:
    a catheter defining a blood vessel insertable end, a remote end, and a lumen passage having a first outlet proximate said insertable end and a second outlet spaced from said insertable end;
    a radiopaque balloon, formed of an elastic material, supported upon said insertable end and coupled to said first outlet of said lumen passage, said radiopaque balloon having at least a portion characterized by radiopaque properties;
    a source of liquid under pressure;
    valve means coupled to said second outlet of said lumen passage and said source of liquid under pressure, said valve means being capable of intercoupling said source of liquid to said second outlet of said lumen; and
    an expandable pressure reservoir having an inflatable elastic balloon,
    said valve means being coupled to said expandable pressure reservoir as well as said second outlet of said lumen passage and said source of liquid under pressure, said valve means being capable of alternatively intercoupling said source of liquid to said expandable pressure reservoir, or intercoupling said source of liquid to said second outlet of said lumen or intercoupling said expandable pressure reservoir to said second outlet of said lumen passage.

6. A catheter assembly as set forth in claim 5 wherein said source of liquid under pressure includes a syringe having a syringe body for receiving a liquid, a coupler coupled to said valve means, and a movable plunger for forcing said liquid from said syringe body through said coupler.

7. A catheter assembly as set forth in claim 6 wherein said catheter further defines a blood bypass forming a blood passage past said radiopaque balloon.

8. A catheter assembly as set forth in claim 7 wherein said catheter defines a center passage extending from said insertable end and wherein said blood bypass includes a bypass port extending through said catheter into said center passage.

9. For use in dilating a constricted blood vessel during angioplasty, athrectomy or other arterial procedures, a vascular catheter assembly comprising:

a catheter defining a blood vessel insertable end, a remote end, and a lumen passage having a first outlet proximate said insertable end and a second outlet spaced from said insertable end;

a radiopaque balloon supported upon said insertable end and coupled to said first outlet of said lumen passage, said radiopaque balloon having at least a portion characterized by radiopaque properties;

a source of liquid under pressure;

valve means coupled to said second outlet of said lumen passage and said source of liquid under pressure, said valve means being capable of intercoupling said source of liquid to said second outlet of said lumen; and an expandable pressure reservoir having an inflatable elastic member, said valve means being coupled to said expandable pressure reservoir as well as said second outlet of said lumen passage and said source of liquid under pressure, said valve means being capable of alternatively intercoupling said source of liquid to said expandable pressure reservoir, or intercoupling said source of liquid to said second outlet of said lumen or intercoupling said expandable pressure reservoir to said second outlet of said lumen passage.

* * * * *